United States Patent [19]

Schwartz

[11] Patent Number: 4,730,631

[45] Date of Patent: Mar. 15, 1988

[54] PROBE WASH STATION

[75] Inventor: Henry L. Schwartz, Los Gatos, Calif.

[73] Assignee: Sequoia-Turner Corporation, Mountain View, Calif.

[21] Appl. No.: 757,742

[22] Filed: Jul. 22, 1985

[51] Int. Cl.⁴ .............................................. B08B 3/04
[52] U.S. Cl. ............................... 134/155; 134/166 R; 134/170; 134/182; 134/201; 141/91; 220/DIG. 6; 422/63
[58] Field of Search .................. 134/182, 166 R, 152, 134/168, 170, 22.18, 154, 201, 186, 64 R, 122 R, 194, 155; 314/23; 137/582, 590; 422/63; 220/DIG. 6; 141/82, 91

[56] References Cited

U.S. PATENT DOCUMENTS

| | | | |
|---|---|---|---|
| 1,105,561 | 7/1914 | Hershey | 134/182 X |
| 1,161,727 | 11/1915 | Randall | 134/182 |
| 1,245,767 | 11/1917 | Randall | 134/182 |
| 1,335,853 | 4/1920 | Myrick | 134/182 |
| 2,619,977 | 12/1952 | Hagen | 134/182 X |
| 2,788,008 | 4/1957 | Wanzer | 134/170 X |
| 3,615,818 | 10/1971 | Ruthner | 134/122 X |
| 3,708,264 | 1/1973 | Jottier . | |
| 3,836,329 | 9/1974 | Jordan . | |
| 3,850,207 | 11/1974 | Loliger et al. | 141/91 X |
| 3,912,535 | 10/1975 | Rauser | 141/91 X |
| 3,951,605 | 4/1976 | Natelson . | |
| 4,053,284 | 10/1977 | Posch . | |
| 4,228,814 | 10/1980 | Luetni et al. | 134/198 X |
| 4,271,123 | 6/1981 | Currey et al. . | |
| 4,298,570 | 11/1981 | Lillig et al. . | |
| 4,366,119 | 12/1982 | Takeuchi . | |
| 4,373,658 | 2/1983 | March et al. | 134/182 |
| 4,399,711 | 8/1983 | Klein . | |
| 4,495,149 | 1/1985 | Iwata et al. . | |
| 4,509,545 | 4/1985 | Trotter | 134/199 |
| 4,517,160 | 5/1985 | Galle et al. . | |
| 4,534,494 | 8/1985 | Hautemont | 141/91 X |
| 4,543,238 | 9/1985 | Mimura et al. | 422/63 |
| 4,554,839 | 11/1985 | Hewett et al. . | |

FOREIGN PATENT DOCUMENTS

| | | |
|---|---|---|
| 69986 | 7/1981 | European Pat. Off. . |
| 5470236 | 12/1980 | Japan . |
| 562560 | 1/1981 | Japan . |

Primary Examiner—Timothy F. Simone
Assistant Examiner—Frankie L. Stinson
Attorney, Agent, or Firm—Limbach, Limbach & Sutton

[57] ABSTRACT

For use with an apparatus for performing biological fluid assays, the apparatus having a probe assembly that includes a tubular probe, a probe wash station for washing the tubular probe with a washing fluid. The probe wash station comprises a probe washing receptacle that is adapted to receive the tubular probe, the receptable having an anti-splash mechanism therein for preventing the splashing of the washing fluid.

7 Claims, 3 Drawing Figures

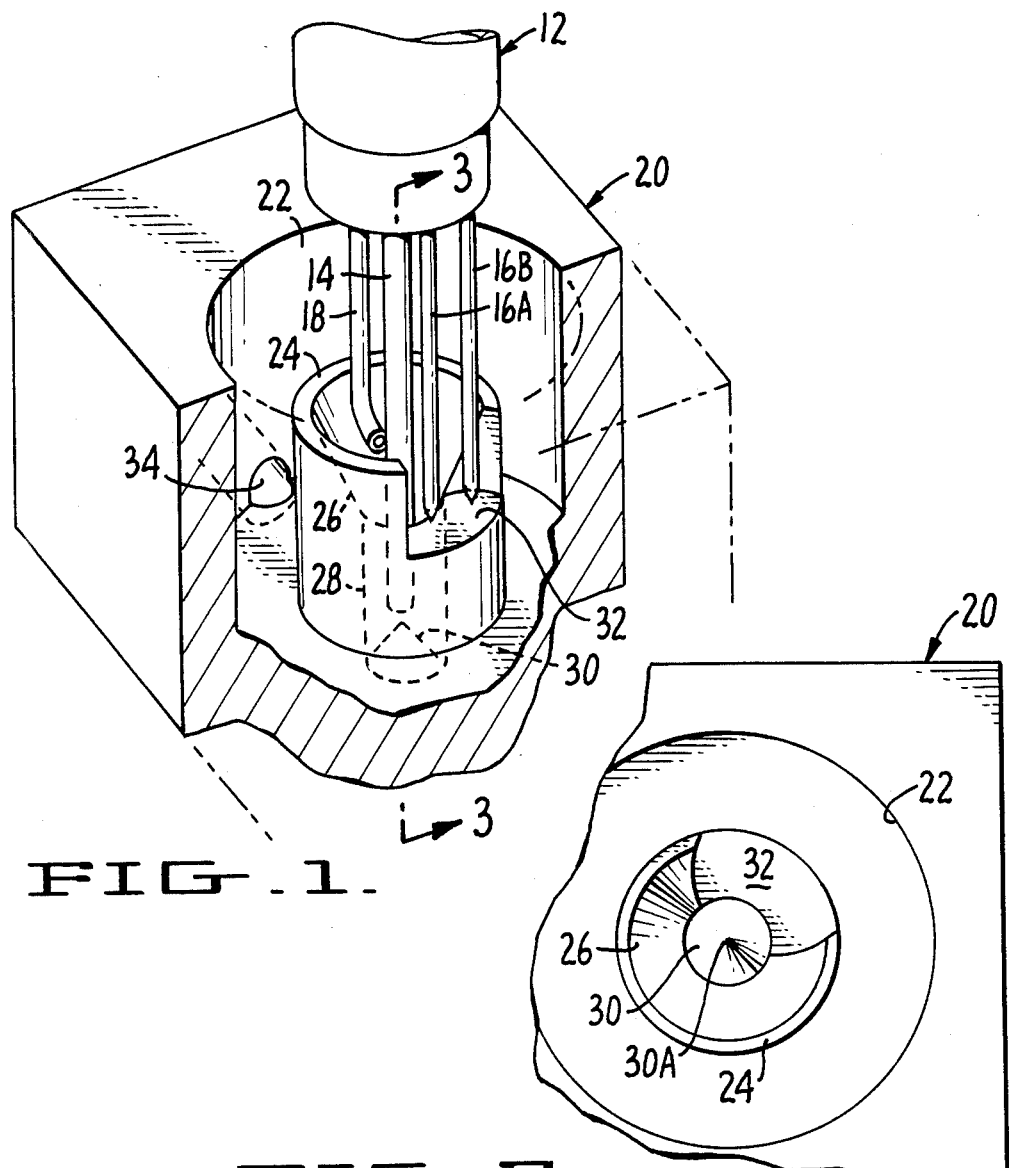
FIG. 1.
FIG. 2.
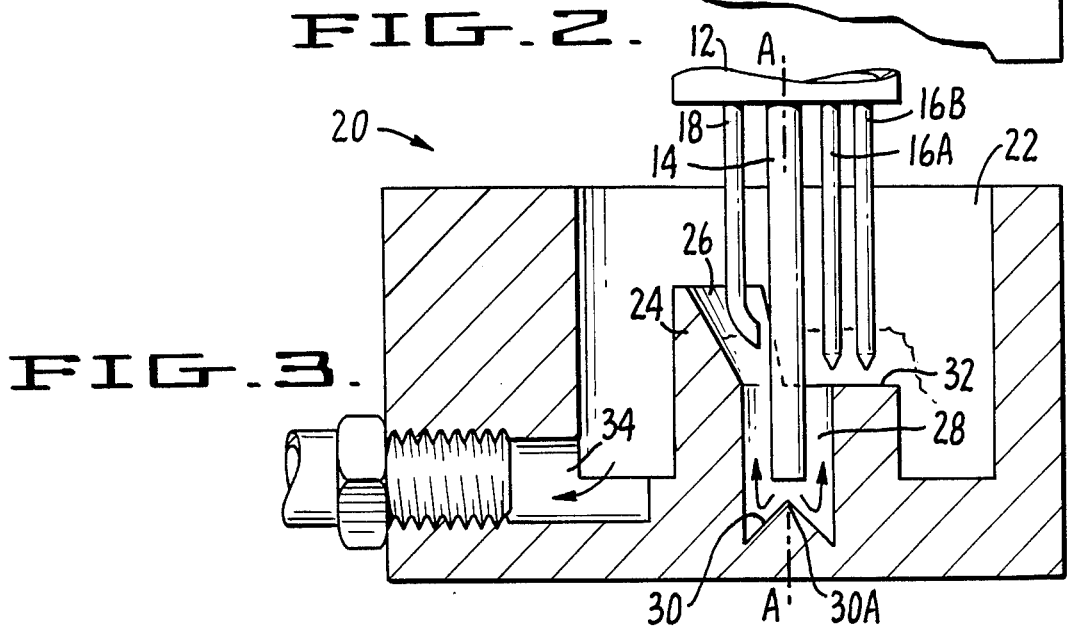
FIG. 3.

PROBE WASH STATION

DESCRIPTION

1. Technical Field

This invention relates to apparatus for performing biological fluid assays, and more particularly, to a probe wash station for such an apparatus.

2. Background Art

Apparatus for performing biological fluid assays are common in the art. Such an apparatus invariably includes a sampling mechanism for aspirating and/or dispensing sample fluids. Tubular probes are generally used to perform the aspiration and dispensation steps. Since these probes are used repeatedly to aspirate and dispense a variety of sample fluids, they must be washed after each sampling so as to prevent the carryover of one sample fluid to the next. A washing mechanism, therefore, must be employed.

Washing mechanisms in the prior art are generally designed such that they are capable of minimizing the splashing of the washing fluid. This capability, however, required the tubular probes to be accurately and precisely positioned in the washing mechanism.

DISCLOSURE OF THE INVENTION

An ideal washing mechanism, however, should be capable of preventing the splashing of the washing fluid without having to restrict the probes to a certain precise position. In addition, since many apparatus include electrodes and other probes which generally come into contact with the sample fluid, they should also be washed in order to prevent contamination of subsequent samples.

It is a major object of the present invention to provide a probe washing station that does not restrict probes to a certain precise position in order to prevent splashing of the washing fluid.

It is another object of the present invention to provide a probe washing station that is capable of washing electrodes and other probes which had come into contact with the sample fluid.

In order to accomplish the above and still further objects, the present invention provides a probe wash station that is used with an apparatus for performing biological fluid assays, the apparatus having a probe assembly that includes a tubular probe. The probe wash station, adapted for washing the tubular probe with a washing fluid, comprises a probe washing receptacle that is adapted to receive the tubular probe, the receptacle having an anti-splash mechanism therein for preventing the splashing of the washing fluid.

Other objects, features, and advantages of the present invention will appear from the following detailed description of the best mode of a preferred embodiment, taken together with the accompanying drawings.

DESCRIPTION OF THE DRAWINGS

FIG. 1 is a perspective view of a probe wash station of the present invention, partially broken away;

FIG. 2 is partial, top view of the probe wash station of FIG. 1; and

FIG. 3 is a side cross section view of the probe wash station of FIG. 1, partial broken away.

BEST MODE FOR CARRYING OUT THE INVENTION

Referring to FIG. 1, there is shown a probe assembly, designated 12. Probe assembly 12 includes a tubular probe 14, two electrodes 16A and 16B, and an auxiliary probe 18. Probe assembly 12 is one component of an apparatus for performing immunonological assays, not shown. The apparatus and its operation are more fully illustrated and described in an application assigned to a common assignee, entitled Method and Apparatus for Performing Automated, Multi-Sequential Immunoassays, Ser. No. 757,676. For washing probes 14 and 18, and electrodes 16A and 16B, a probe wash station of the present invention is provided, designated 20.

Probe wash station 20 is a generally rectangular member that has a generally cylindrical well-like receptacle 22 in which a washing reservoir 24 is positioned. Washing reservoir 24 comprises a frustoconical top portion 26 and a cylindrical lower portion 28. At the base of cylindrical lower portion 28 is an anti-splash mechanism 30. Anti-splash mechanism 30 in the preferred embodiment is a conical member. Conical member 30 has its apex 30A facing tubular probe 14, as described below. Washing reservoir 24 also comprises a washing platform 32. Probe wash station 20 also includes an outlet 34 that is in communication with receptacle 22.

In use, tubular probe 14 of assembly 12 first aspirates and dispenses a sample fluid, not shown. After moving and positioning itself above probe wash station 20, assembly 12 then lowers itself into station 20. As best shown in FIGS. 1 and 3, tubular probe 14 is positioned in cylindrical lower portion 28, slightly removed from apex 30A of conical member 30. In addition, electrodes 16A and 16B are positioned above washing platform 32.

A washing solution is then forcibly dispensed through tubular probe 14. This action removes traces of the sample fluid that are adhered to the interior surface of probe 14. The washing solution, when it exits probe 14 and impacts conical member 30, does not splash itself to the various surrounding areas of wash station 20. At this stage, the washing fluid is entrained with traces of the sample fluid such that the washing fluid could contaminate the surrounding areas. The desire to minimize or eliminate the splashing of washing fluid is a goal recognized by those skilled in the art.

In prior art washing mechanisms, counterparts to cylindrical lower portion 28 generally have either a flat base or conical base, i.e., the apex of the base is pointed away from tubular probe. When the base of a cylindrical lower portion has one of these configurations, the tubular probe must be positioned precisely on the axis of the cylindrical lower portion so as to prevent splashing. Unbeknownst to those skilled in the art, the inventor has discovered that conical member 30, with its apex 30A pointing toward tubular probe 14, eliminates splashing of the washing fluid even when probe 14 is not aligned with the axis "A" of cylindrical lower portion 28, which is also the axis of conical member 30. When probe 14 is positioned not directly above apex 30A of conical member 30, but rather facing the inclined surface of conical member 30, splashing still does not occur. Thus, contrary to the prior art requirement that the tubular probe must be aligned with the axis of the cylindrical lower portion in order to prevent splashing, such a restriction is not required for probe 14 of probe wash station 20.

The exiting washing fluid then circulates and foams about inside cylindrical lower portion 28, thereby washing the exterior surface of probe 14 that is inside lower portion 28. The turbulent washing fluid then exits washing reservoir 24 via washing platform 32. This action removes traces of the sample fluid that may have been adhered to electrodes 16A and 16B. Top portion 26, having its frustoconical configuration, assists the flow of the washing fluid over washing platform 32 so as to clean electrodes 16A and 16B. Further, washing reservoir 24 is also capable of receiving other probes that may be part of probe assembly 12, e.g., auxiliary probe 18. The circulating and turbulent action of washing fluid is capable of washing auxiliary probe 18, as best shown in FIG. 3. The washing fluid then exits probe wash station 20 via outlet 34. The exiting washing fluid is commonly aspirated into a vacuum waste bottle.

In the preferred embodiment, washing reservoir 24 has a diameter of approximately 0.81 inch and the larger diameter of frustoconical upper portion 26 approximately 0.40 inch. The smaller diameter of upper portion 26, which is also the diameter of cylindrical lower portion 28, is approximately 0.38 inch. The angle of the frustoconical inclination is approximately 60°, and the angle of conical member 30 is approximately 45°. Further, the relative length of probes 14 and 18 and electrodes 16A and 16B are as follows: probe 14 is approximately 1/16 inch longer than the length of electrodes 16A and 16B, and probe 18 approximately ⅛ inch shorter than the length of electrodes 16A and 16B.

It will be apparent to those skilled in the art that various modifications may be made within the spirit of the invention and the scope of the appended claims.

I claim:

1. For use with an apparatus for performing fluid analyses, said apparatus having a probe assembly that includes a primary probe and at least one auxiliary probe juxtaposed to said primary probe, a probe washing station for washing said primary probe and said auxiliary probe with a washing fluid, comprising
   a washing reservoir that comprises a frustoconical top portion and a cylindrical lower portion, said cylindrical lower portion being adapted to receive said primary probe and to retain a volume of washing fluid in which to partially immerse the primary probe; and
   a washing platform that is adapted to assist in the washing of said auxiliary probe, wherein
   the cylindrical lower portion of the reservoir includes a conical member positioned at the base of said lower portion with its apex proximate to said primary probe in order to prevent splashing of said washing fluid that is exiting said primary probe.

2. The probe wash station as claimed in claim 1, wherein said conical member maintains its anti-splashing characteristic even when said primary probe is misaligned with the axis of said conical member.

3. The probe wash station as claimed in claim 2, wherein the circulation of said washing fluid in said cylindrical lower portion washes the exterior of said primary probe.

4. The probe wash station as claimed in claim 3, wherein the flow of said washing fluid over said washing platform performs said washing of said auxiliary probe.

5. The probe wash station as claimed in claim 4, further comprising
   an outlet for permitting the exit of said washing fluid from said probe wash station.

6. For use with an apparatus for performing fluid analyses, said analytical apparatus having a probe assembly that includes a probe,
   a probe wash station for washing said probe with a washing fluid comprising:
   a probe washing receptacle that is adapted to receive said probe and to retain a sufficient volume of washing fluid in which to partially immerse the probe; and
   an anti-splash mechanism contained within said probe washing receptacle for preventing the splashing of wash fluid which is dispensed from said first probe, said anti-splash mechanism being a conical member positioned at the base of said receptacle with the apex of said conical member proximate to said probe.

7. For use with an apparatus for performing fluid analyses, said analytical apparatus having a probe assembly that includes a first probe and at least one auxiliary probe that is juxtaposed to said first probe,
   a probe wash station for washing said probes with a washing fluid comprising:
   a probe washing receptacle that is adapted to receive said probes and to retain a sufficient volume of washng fluid to partially immerse at least the first probe; and
   an anti-splash mechanism contained within said probe washing receptacle for preventing the splashing of wash fluid which is dispensed from said first probe, said anti-splash mechanism being a conical member positioned at the base of said receptacle with the apex of said conical member proximate to said first probe.

* * * * *